United States Patent [19]

Yonkers et al.

[11] Patent Number: 4,599,220
[45] Date of Patent: Jul. 8, 1986

[54] MULTI-CHANNEL PIPETTER

[76] Inventors: Edward H. Yonkers, 16 Walnut St., Watertown, Mass. 02172; James Ryan, 38 Satuit Trail, Scituate, Mass. 02066

[21] Appl. No.: 638,503

[22] Filed: Aug. 7, 1984

Related U.S. Application Data

[63] Continuation of Ser. No. 348,876, Feb. 16, 1982, abandoned.

[51] Int. Cl.⁴ .............................................. B01L 3/02
[52] U.S. Cl. .................................... 422/100; 73/864.17
[58] Field of Search ............... 422/100; 73/864.18, 73/864.02, 864.16, 864.17, 864.25

[56] References Cited

U.S. PATENT DOCUMENTS

| 3,656,351 | 4/1972 | Raczak | 73/864.18 |
| 3,945,254 | 3/1976 | Rebold | 73/864.16 |
| 3,954,014 | 5/1976 | Andrews | 73/864.16 |
| 4,009,611 | 3/1977 | Kotter | 73/864.17 |
| 4,215,092 | 7/1980 | Suozariemi | 422/100 |
| 4,257,268 | 3/1981 | Pepirelli | 73/864.17 |

FOREIGN PATENT DOCUMENTS 3008347  10/1980  Fed. Rep. of Germany ...... 422/100

Primary Examiner—Hiram H. Bernstein

[57] ABSTRACT

A multi-channel pipetter having a case generally in the form of a pistol grip. A block having a plurality of cylinders is mounted in the case adjacent the bottom and a piston plate is mounted for reciprocal motion in the case with its pistons in the cylinders. A finger actuated slide in the case engages the plate and moves the pistons so as to fill and discharge the contents of the cylinders.

18 Claims, 6 Drawing Figures

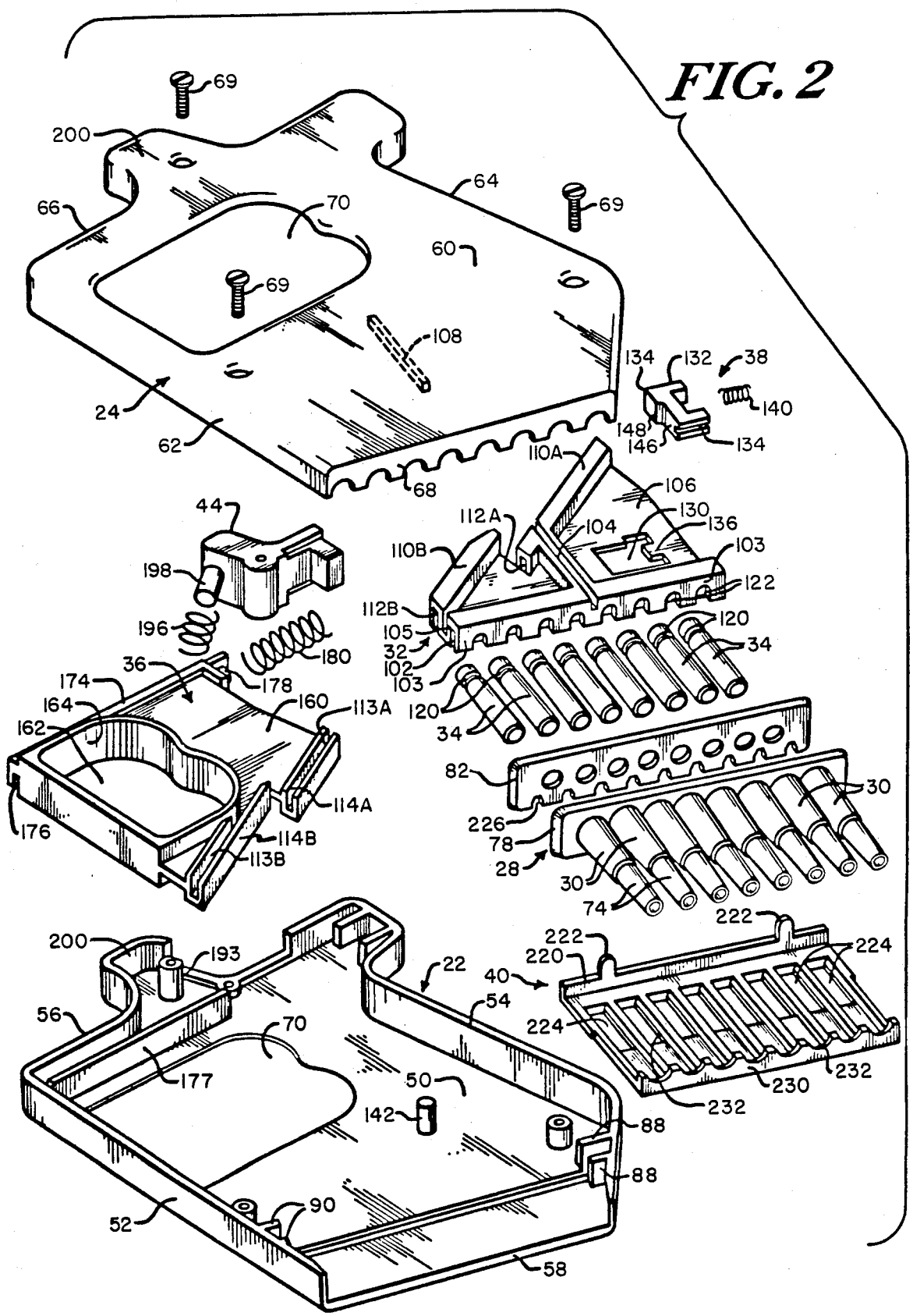

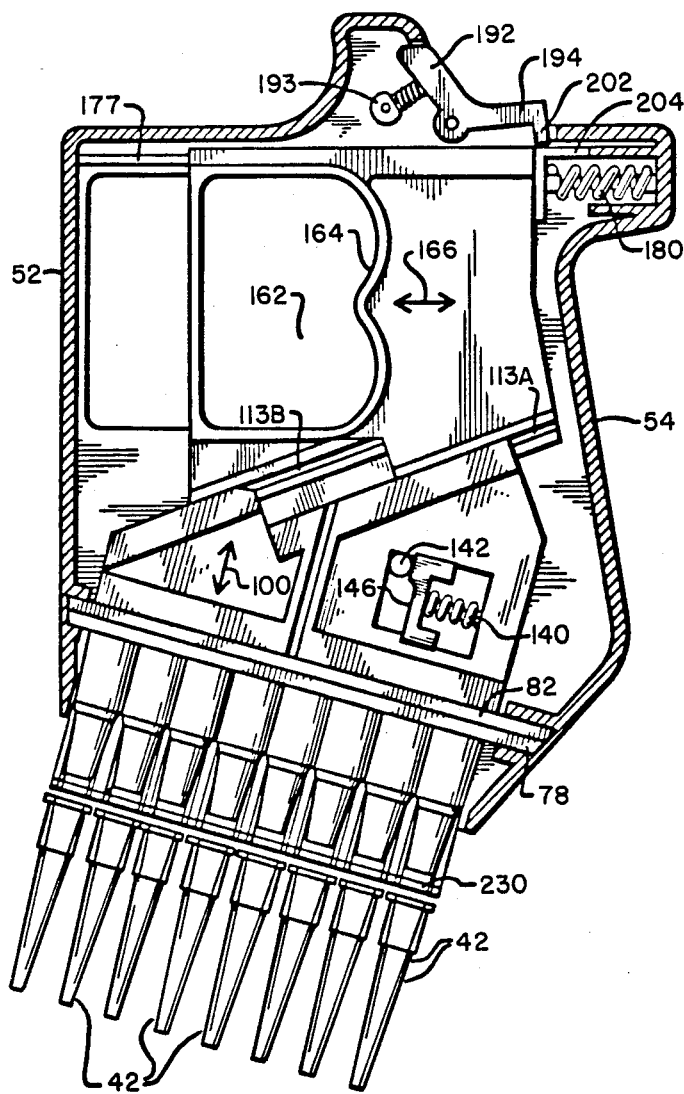
FIG. 6
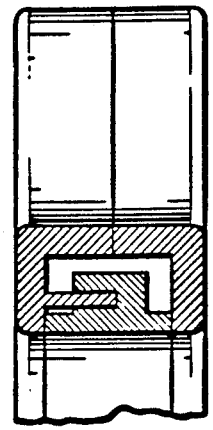
FIG. 3
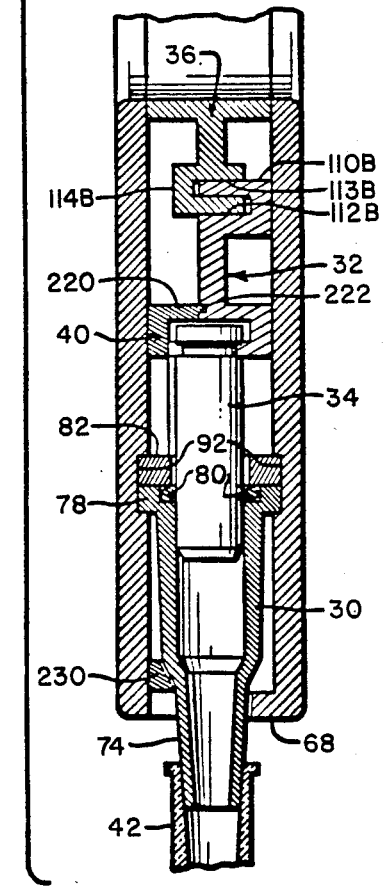

MULTI-CHANNEL PIPETTER

This application is a continuation of application Ser. No. 348,876, filed Feb. 16, 1982, now abandoned.

BACKGROUND OF THE INVENTION

This invention relates to pipetting and more particularly comprises a new multi-channel pipetter. The pipetter is particularly designed to fill the wells of a multi-well plate used for a variety of tests and experiments in the laboratory.

Presently, only large and cumbersome apparatus are available for performing the pipetting necessary when using multi-well plates. The apparatus is typically bulky and difficult to use. The problems associated with the apparatus stem in large part from the fact that the designs have not been human engineered. These devices require that an operator simultaneously hold, aim and operate them, and the prior art devices are difficult to manage with accuracy and precision while measuring and pipetting milliliters of fluid. As a result, the tests and experiments pipetted with standard apparatus are sometimes adversely affected. Furthermore, the pipetters presently available are expensive due to the use of precision machined elements.

SUMMARY OF THE INVENTION

A principal object of the present invention is to provide a multi-channel pipetter human engineered for ease and accuracy of operation.

Another important object of the present invention is to provide a multi-channel pipetter having fine control for the filling operation to enhance filling accuracy. Another object of the present invention is to provide a multi-channel pipetter made primarily of molded and relatively inexpensive parts and which is easily assembled so as to be inexpensive to manufacture.

Still another object of the present invention is to provide a multi-channel pipetter which is easily aimed to enhance filling accuracy.

Yet another object of the present invention is to provide a multi-channel pipetter incorporating the use of disposable tips and an automatic tip ejector, which is easy and convenient to operate.

To accomplish these and other objects, the multi-channel pipetter of this invention comprises a case including front and back walls which have an enlarged finger opening adjacent to the top end of the case. A block is mounted in the case below the finger opening. Formed in the block are a plurality of parallel cylinders which extend in a downward direction below the lower end of the case. Each cylinder is shaped to enable a disposable tip to be slipped onto its lower end. A piston plate is mounted in the case such that it moves in a reciprocal fashion parallel to the axis of the cylinder. The piston plate is mounted in the case below the finger opening. The piston plate includes a plurality of pistons that extend into the cylinders. The pistons move axially within the cylinders when the piston plate is reciprocated. The piston plate moves in response to movement of a finger actuated slide due to the interaction of inclined surfaces on both the slide and piston plate. A stripper plate is connected to the piston plate and has a flange at its lower end which slides along the lower end of the outside of the cylinders. When the piston plate is reciprocated to its lowermost position the stripper plate ejects tips which are mounted on the lower ends of the cylinders. The case includes a stop which prevents the finger actuated slide from inadvertently moving the piston plate to the lowermost position. The case also has mounted therein a detent assembly which is connected to the piston plate and tactily indicates to the operator that the pistons have been displaced in the cylinders through a predetermined volume.

These and other objects and features of the present invention will be better understood and appreciated from the following detailed description of one embodiment thereof, selected for purposes of illustration and shown in the accompanying drawings.

BRIEF FIGURE DESCRIPTION

FIG. 2 is an exploded view of the pipetter of FIG. 1;

FIG. 3 is a cross sectional view of the assembled pipetter taken along the section line 3—3 in FIG. 1;

FIG. 6 is a side view similar to FIG. 4 and with the slide actuator in its fully retracted position to eject the removable tips.

DETAILED DESCRIPTION

Figure 1:
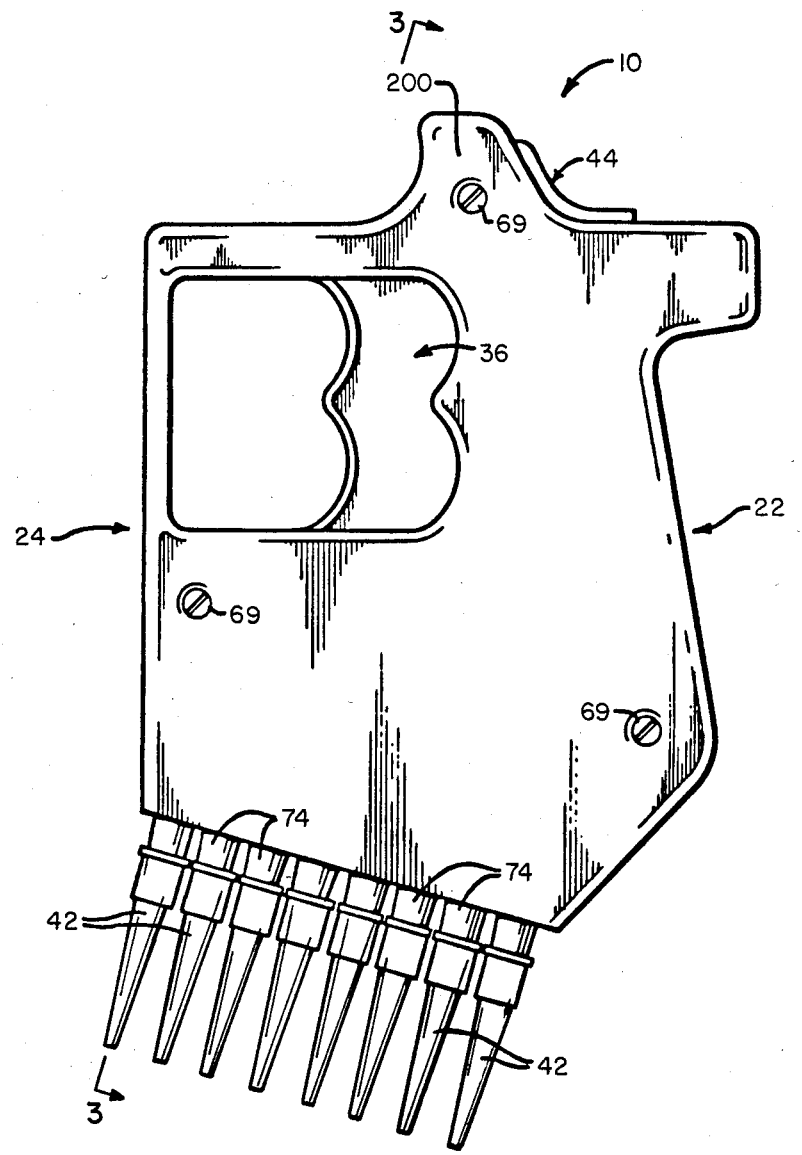
FIG. 1 is a side view of a multi channel pipetter constructed in accordance with this invention.

The pipetter 10 shown in the drawing includes a pistol grip-shaped case 20 composed of a base 22 and cover 24 that together define a wide but slim chamber 26 within which are mounted the various components of the device. The major components include a cylinder block 28 having a plurality of cylinders 30, a piston plate 32 carrying an array of pistons 34 which extend into the cylinders 30, and finger actuated slide 36. A volume control assembly 38 provides a tactile signal to the operator as the pipetter is operated. The assembly also includes a stripper plate 40 for removing the disposable filler tips 42 mounted on the cylinders and a release button 44 which limits the motion of the slide to control the operation of the stripper plate 40. The various parts of the assembly are described in greater detail below.

The base 22 which forms a tray on which the major parts are assembled includes a support wall 50, a front flange 52 and rear flange 54. The flanges 52 and 54 diverge downwardly slightly at an angle of approximately 10° to form the pistol grip configuration of the case. A flange 56 extends along the top edge of the base while the bottom edge 58 is free of any flange or rim.

The cover 24 is essentially a mirror image of base 22 and includes front wall 60, front flange 62, rear flange 64 and top flange 66. The lower edge of the cover is also provided with a flange 68 that has a scalloped configuration to support the cylinders 30 of block 28 as described below. When the case is assembled by means of the through screws 69, the various flanges of the base and cover abut one another to enclose chamber 26. Finger openings 70 and 72 are respectively provided in the base and cover to provide access to the slide 36 which forms the trigger for the pipetter.

Cylinder block 28 disposed in the lower portion of the chamber 26 is formed with a number of parallel cylinders 30 having downwardly tapered nozzles 74 that extend out of chamber 26 and register with the semi-circular slots 76 formed in flange 68 on cover 24. The cylinders which are integrally formed with plate 78 each carry an o-ring 80 in a seat provided in plate 78 about the top of each cylinder (see FIG. 3). The several o-rings are sandwiched in position by retainer 82 which lies face to face with plate 78. Plate 78 and retainer 82 in turn are held in place within the chamber 26 by the opposed pairs of flanges 88 and 90 in the base and cover. Shallow recesses 92 are also provided in the base and cover, which receive the long edges of the plate 78 and retainer 82 as shown in FIGS. 2 and 3.

Figure 5:
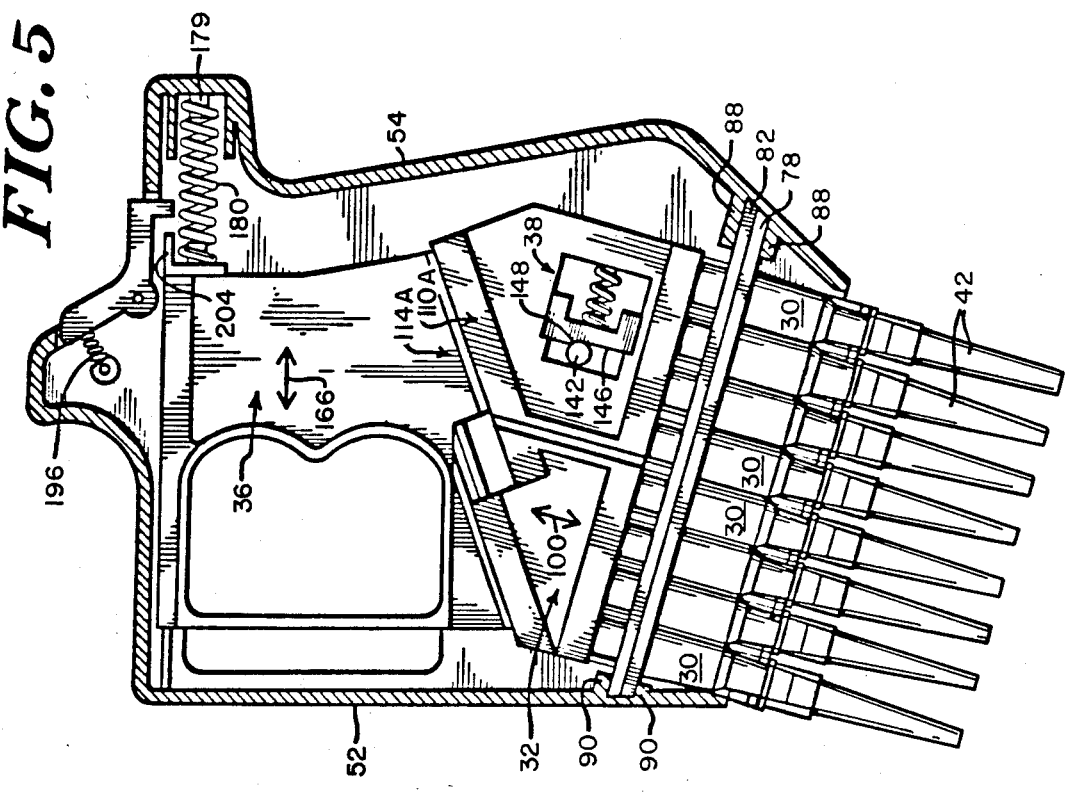
FIG. 5 is a side view similar to FIG. 4 and with the slide actuator in its first retracted position which it assumes when the pipetter is about to be filled and when its contents have been discharged.
Figure 4:
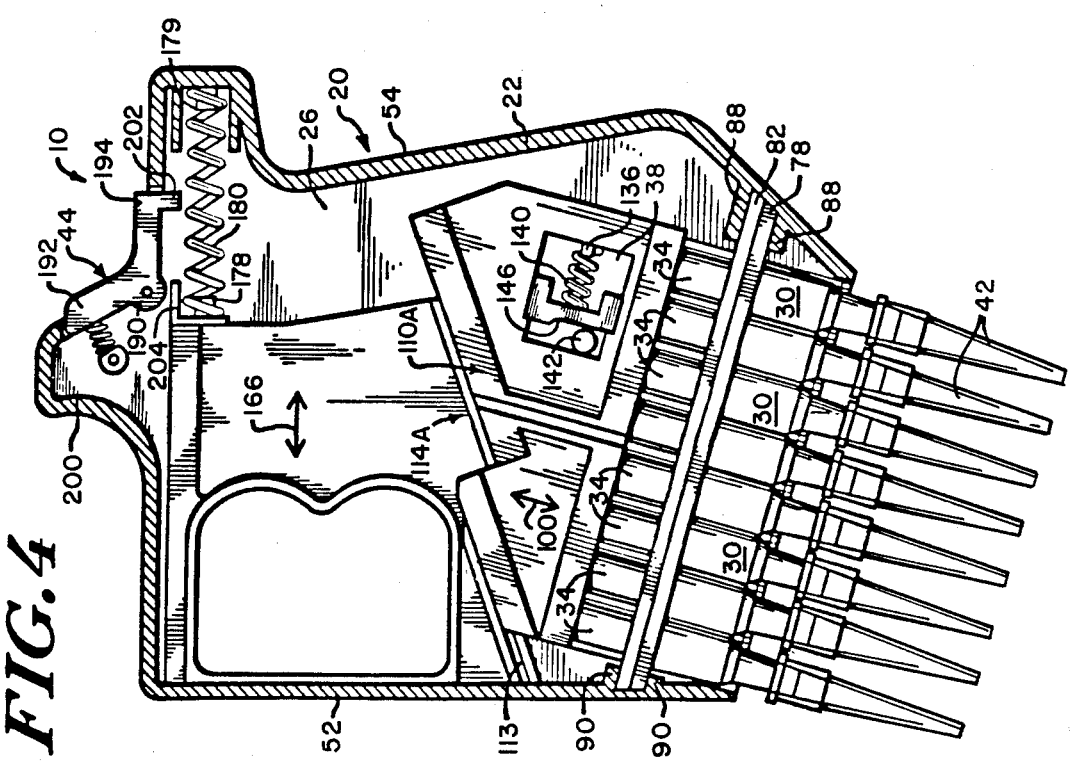
FIG. 4 is a side view of the pipetter and with the cover removed and with the slide actuator in its biased or unactuated position.

Piston plate 32 mounted in chamber 26 is positioned to reciprocate within the chamber as suggested by double arrow 100 in FIGS. 4–6. The plate has a lower channel 102 defined by flanges 103 and 105 parallel to plate 78 and retainer 82 of the cylinder assembly, and the channel carries the pistons 34 that extend into the cylinders, as shown in FIGS. 2 and 3. The plate 32 is guided for reciprocal motion in chamber 26 by a slot 104 formed in its front face 106 that registers with rib 108 on the inner surface of wall 60 of the cover.

The upper edges 110A and 110B of piston plate 32 are disposed at an angle of approximately 35° with the center line of slot 104. The upper edges 110A and 110B are channeled at 112A and 112B respectively as clearly shown in FIGS. 2 and 3 so as to engage respectively the similarly configured channels 113A and 113B in the lower edges 114A and 114B of the finger actuated slide 36 to maintain the operative connection between the slide and plate as well as transfer motion of the slide to the piston plate. The stepped configurations of the upper edges 110A and 110B of the piston plate and lower edge of the slide enables the connection between them to clear the lower edges of the finger openings 70 and 72 in the base and cover respectively. It will be noted in FIGS. 4–6 that the piston plate is not exposed in the openings.

The pistons 34 may either be formed as an integral part of the piston plate or as separate parts subsequently fastened to the plate. In the embodiment shown, the pistons are separately fabricated and each includes a collar 120 at its top which fit into the recesses 122 in the flange 103 of the plate.

A generally rectangular opening 130 is formed in the main panel of piston plate 32, which houses the volume control assembly 38. The assembly 38 includes a U-shaped slide 132 designed to reciprocate in opening 130 and guided in its motion by the side edges 134 of the slide in cooperation with the side edges of opening 130. A boss 136 formed along the right side of opening 130 as viewed in FIG. 2 carries a compression spring 140 that bears against the slide 132 so as to urge the slide to the left as viewed in FIGS. 4–6. A post 142 is mounted on the wall 50 of base 22 and extends across the path of the slide 132 so as to limit the travel of the slide to the left under the influence of spring 140. The post bears against the front face 146 of the slide.

As the piston plate 32 is reciprocated along the path suggested by arrow 100, face 146 of the slide 132 slides over post 142. A step 148 interrupts the face 146, and therefore, as the slide moves downwardly with downward movement of the piston plate, the step 148 engages post 142 and creates resistance to further downward travel of the piston plate. Because compression spring 140 is yieldable and allows the slide to move to the right as the step 148 engages the post, further downward travel of the piston plate is not prohibited, but rather a tactile signal is given to the operator which indicates a particular position for the plate. That is, the operator of the pipetter is provided a signal by the shoulder 148 cooperating with the post 142 to indicate the volume of displacement of the pistons 34 in the cylinders 30. The manner in which that signal is used is described below in connection with the operation of the pipetter.

Finger actuated slide 36 includes a flat plate 160 with a finger grip opening 162 that extends through the plate and which corresponds in shape to the openings 70 and 72 in the base and cover 22 and 24, respectively. A flange 164 surrounds opening 162 so as to provide protection for the fingers of the user when inserted through the opening to actuate the pipetter. The slide is designed for reciprocal motion in chamber 26 in the direction suggested by double-headed arrow 166 in FIGS. 4–6. The lower edges 114A and 114B of slide 36 are stepped in the same fashion as the upper edge of piston plate 32, and lower edges 114A and 114B are provided with channels edges 113A and 113B respectively which join the complementary channels 112A and 112B along 110A and 110B in piston plate 32.

The upper edge 174 of the slide 36 is provided with a slot 176 that receives rib 177 formed in base 22 to retain the slide in place and limit its movement to the reciprocal motion suggested by arrow 166. A boss 178 at the rear of slide 36 carries a compression spring 180 disposed in channel 179 in base 22 so as to bias the slide to the left as viewed in FIGS. 4–6. The slide, of course, may be moved against the bias of the spring to the right as shown in FIGS. 5 and 6, which through the cooperation of the inclined mating edges of the slide and piston plate causes the piston plate to move downwardly in chamber 26.

Release button 44 is pivotally supported in the top of chamber 26 by pin 190 that extends between the base and cover. The button 44 has two arms 192 and 194 that blend smoothly into the edge of the case. A short compression spring 196 mounted on post 198 on arm 192 bears against peg 193 to yieldably urge the button to turn clockwise as viewed in FIGS. 4–6 to assume the position shown in FIGS. 5 and 6. It will be noted that arm 194 of the button carries a stop 202 that extends into the path of travel of projection 204 carried at the upper rear corner of the slide 36. The stop 202 when positioned as shown in FIGS. 4 and 5 limits the extent to which the slide may be retracted against the bias of spring 180. The stop 202 may be disabled by pressing against the arm 192 of the button causing the button to turn counterclockwise against the bias of spring 196. This action moves the stop 202 out of the path of travel of projection 204 so as to enable the slide to be retracted fully to the right as viewed in FIG. 6.

Stripper plate 40 is carried on the lower portion of piston plate 32 and moves with the plate reciprocally in the direction of double arrow 100. The stripper plate is generally rectangular in shape and has a flange 220 along its upper edge which engages the rear side of the bottom of piston plate 32. The stripper plate is held in place on the piston plate by tabs 222 that may be cemented or otherwise secured to mating slots appropriately provided in the piston plate. The front face of plate 40 is provided with arcuate grooves 224 that receive the sides of the cylinders 30. The margins of the troughs 224 slide within notches 226 provided in the side edge of plate 78 and retainer 82 (the notches are seen only in the plate 82 in FIG. 2), and the lower edge of stripper plate carries a foot 230 also provided with shallow notches 232 designed to surround the nozzle portions 74 of the cylinders 28. The foot 230, as the stripper plate moved downwardly, is designed to engage the upper edges of the removable tips 42 to strip the tips from the nozzles 74.

As mentioned in the introduction, the pipetter of this invention is particularly designed to fill the wells of a 96 well plate used for a variety of tests and experiments in the laboratory. These plates have 12 rows of 8 wells each, and the pipetter of this invention enables the user to simultaneously fill all of the wells in one row. By repeating the operation 12 times, all 96 wells may be filled. The user holds the pipetter's pistol grip shaped case with two fingers (either the index and middle finger or middle and forefinger extending through the openings 70 and 72 in the case 20 and engaging the slide 36. The palm surrounds the case and bears against the edges 54 and 64 of the base and cover so that the entire case is held as a pistol grip in the hand with the thumb extending to the back side. Conventionally, disposable tips 42 are slipped onto the nozzles 74 of each of the cylinders to enable the pipetter to readily take up and subsequently expel the fluid to be placed in the various wells of the tray. With the pipetter empty, the user squeezes the trigger defined by the finger slide 36 which causes the slide to be moved to the right, and the piston plate to move downwardly so that the pistons 34 extend a substantial distance into the cylinders. This squeezing motion is continued until the user detects resistance created by the shoulder 148 of the volume control as it engages the post 142. This position is shown in FIG. 5. The particular slide 132 is selected having the notch 148 so positioned as to create a specific desired volumetric displacement of the pistons in the cylinders when the shoulder 148 engages the post 142 to create this additional resistance. With the finger slide moved to that position, the user then places the lower ends of the tips 42 into the solution to be sucked up by the pipetter and later transferred to the wells. The operator then releases the finger slide which allows the slide to move under the influence of the spring 180 to its extreme biased position shown in FIG. 4, which retracts the pistons 34 from the cylinders 28 so as to create a vacuum to draw the solution into the cylinders.

The user then, holding the pipetter as a pistol grip, aligns the bottoms of the tips 42 with the row of wells to be filled. The user then again squeezes the trigger and moves the finger slide to the right until resistance once again is encountered by contact of the shoulder 148 of the volume control with the post 142. This action discharges the contents of the cylinders into the wells. To ensure complete discharge of the solution in the cylinders, the user squeezes the trigger so as to cause the piston slide to move downwardly and cause the shoulder 148 to pass the post 142. This is permitted as the spring 140 compresses and allows the slide 132 to move to the right. It will be noted in FIG. 5 that the stop 202 does not engage the projection 204 when the shoulder 148 engages the post 142 so that this additional squeezing of the slide is permitted. By moving the slide fully rearwardly until the projection 204 engages the stop 202, complete discharge of the contents is assured. This procedure may be repeated over and over again until all of the rows of wells are filled.

When the user desires to dispose of the tips 42, it is only necessary to depress the release button 44 against the bias of spring 196 so as to remove the stop 202 from the path of travel of the projection 204. With the button depressed, the user may retract the finger slide all the way to the right as shown in FIG. 6, which will cause the foot 230 of the stripper plate to bear against the upper edges of the tips 42 and push them off the nozzles 74.

From the foregoing description, the various advantages of this invention will be fully appreciated. First, it will be appreciated that virtually all of the parts with the exception of the springs, may be injection molded of plastic material and therefore virtually all machined parts may be eliminated. Consequently, the cost of manufacture of the various parts is rather modest. Second, the pipetter is not bulky and is human engineered so as to be designed for comfortable use. The case of the pipetter fits comfortably within the hand, can be held by one hand, and rather than being awkward, is very natural to use. The short tips 72 that extend below the bottom of the grip configuration of the case make it very easy for the user to align the tips with the wells in the plate. Because the tips, by virtue of the configuration of the cylinders, extend slightly forward away from the operator as well as down from the bottom of the grip, it is easy for the user to aim the tips at the wells and to observe their position. The cylinders are disposed at an angle of approximately 20° with the vertical center line of the case. The device also enables the user to eject the disposable tips with the same stroke as used to fill and discharge the cylinders. At the same time, the positive stop prevents accidental ejection of the tips. The release button 44 can be actuated either with the thumb of the hand holding the pipetter or alternatively can be conveniently actuated by the other hand.

Another important advantage of the present invention is the fine control provided over the filling operation because of the relatively large stroke of the finger slide as compared to the distance of reciprocal travel of the piston plate derived from the angular relationship of the slide and piston plate. In the preferred embodiment illustrated, the angle of the mating edges of the piston plate and finger slide with the line of travel of the piston plate is approximately 55°. Consequently, the ratio of slide stroke to piston stroke is more than two to one. This large slide stroke enables the operator to very precisely control the operation of the pistons in the cylinders to draw solution into them.

Having described the invention in detail, those skilled in the art will appreciate that numerous modifications may be made of this invention without departing from its spirit. Therefore, it is not intended to limit the breadth of this invention to the single embodiment illustrated and described. Rather, it is intended that the scope of this invention be determined by the appended claims and their equivalents.

What is claimed is:

1. A multi channel pipetter comprising:
    a case having a support wall and an enlarged finger opening through the support wall adjacent the top end thereof,
    a block mounted in the case below the opening and having a plurality of parallel cylinders formed therein, said cylinders extending downwardly below the lower end of the case and each cylinder being shaped to enable a filler tube to be slipped onto its lower end,
    a piston plate mounted for reciprocal motion in the case parallel to the axes of the cylinders and below the opening, said plate carrying a plurality of pistons which extend into the cylinders and move axially therein when the plate is reciprocated, a finger actuated slide mounted in the case in alignment with the opening and reciprocally movable in the case along a path forming an acute angle with the path of the piston plate, inclined surfaces on the slide and piston plate and engaging one another causing movement of the slide to move the pistons in the cylinders, a stripper plate connected to the piston plate and having a flange at its lower end which slides along the lower end of the cylinders for ejecting filler tips mounted on the lower end of the cylinders when the piston plate is at its lowermost position, a stop mounted in the case for selectively preventing the slide from moving the piston plate to said lowermost position, and a detent assembly mounted in the case and connected to the piston plate for indicating to the user through the tactile sense that the pistons have been displaced in the cylinders through a selected volume.

2. A multi-channel pipetter as defined in claim 1 further characterized by:

said case having a side edge cooperating with the opening to form a pistol grip configuration for the case to facilitate actuation of the slide through the opening.

3. A multi-channel pipetter as defined in claim 2 further characterized by:

a spring in the case engaging the slide biasing it to a position wherein the pistons are elevated in the cylinders.

4. A multi-channel pipetter comprising:

a case having a support wall and an enlarged finger opening through the support wall adjacent the top end thereof, a block mounted in the case below the opening and having a plurality of parallel cylinders formed therein, said cylinders extending downwardly below the inner end of the case and each cylinder being shaped to enable a filler tube to be slipped onto its lower end, a piston plate mounted for reciprocal motion in the case parallel to the axes of the cylinders and below the opening, said plate carrying a plurality of pistons which extend into the cylinders and move axially therein when the plate is reciprocated, a finger actuated slide mounted in the case in alignment with the opening and reciprocally movable in the case along a path forming an acute angle with the path of the piston plate, inclined surfaces on the slide and piston plate and engaging one another causing movement of the slide to move the pistons in the cylinders, a stripper plate connected to the piston plate and having a flange at its lower end which slides along the lower end of the cylinders for ejecting filler tips mounted on the lower end of the cylinders when the piston plate is at its lowermost position, a stop mounted in the case for selectively preventing the slide from moving the piston plate to said lowermost position, a detent assembly including a post mounted in fixed position in the case and a follower carried by the piston plate which runs over the post as the plate reciprocates, and a step in the follower which engages the post as the piston plate is reciprocated for varying the load on the slide for indicating the displacement of the pistons.

5. A multi-channel pipetter as defined in claim 2 further characterized by:

the axes of the cylinders forming an angle of approximately 20° with the vertical so that the cylinders extend downwardly and away from the operator.

6. A multi-channel pipetter comprising:

a case, a plurality of cylinders in the case with their axes parallel to one another, a piston plate movably mounted in the case and carrying a plurality of pistons that reciprocate in the cylinders upon reciprocation of the plate, a finger actuated slide movably mounted on the case at an angle to the path of motion of the piston plate, and inclined surfaces on the slide and piston plate and engaging one another causing movement of the slide to move the pistons in the cylinders.

7. A multi-channel pipetter as defined in claim 6 further characterized by:

tactile signaling means mounted in the case for indicating the volumetric displacement of the pistons in the cylinders as they are moved by the slide.

8. A multi-channel pipetter as defined in claim 6 further characterized by:

said cylinders extending out of the case and having lower ends tapered to receive filler tips, and a stripper mounted on the case and movable with the piston plate for stripping the tips from the cylinders upon actuation of the slide to an extreme position.

9. A multi-channel pipetter as defined in claim 6 further characterized by:

biasing means in the case operatively connected to the slide for urging the slide in a first position wherein the pistons are retracted in the cylinders, said biasing means being overcome by finger actuation of the slide to move the slide to a second position wherein the pistons extend a substantial distance into the cylinders to expel the contents of the cylinders.

10. A multi-channel pipetter as defined in claim 9 further characterized by:

said cylinders extending out of the case and having lower ends tapered to receive filler tips, and a stripper mounted on the case and movable with the piston plate for stripping the tips from the cylinders upon actuation of the slide to an extreme position beyond the second position away from the first position.

11. A multi-channel pipetter as defined in claim 10 further characterized by:

tactile signaling means mounted in the case for indicating the volumetric displacement of the pistons in the cylinders as they are moved by the slide.

12. A multi-channel pipetter as defined in claim 10 further characterized by:

a releasable stop mounted on the case for selectively preventing the slide from moving from the second to the extreme position.

13. A multi-channel pipetter as defined in claim 11 further characterized by:

said case being in the form of a pistol grip and with an opening through the case within which the finger actuatable slide is exposed.

14. A pipetter comprising:
a case and at least one cylinder in the case,
a piston plate movably mounted in the case and carrying a piston for each cylinder, said plate reciprocating the piston in the cylinder when the plate is moved in the case,
a finger actuated slide mounted for sliding movement on the case at an angle to the path of movement of the piston plate,
and inclined surfaces on the slide and piston plate and engaging one another causing movement of the slide to move the pistons in the cylinders.

15. A pipetter as defined in claim 14 further comprised by:
said case being shaped in the form of a pistol grip, and said cylinder extending out of the case at the bottom of the grip.

16. A multi-channel pipetter as defined in claim 11 further characterized by:
said cylinders extending out of the case at the bottom of the grip.

17. A multi-channel pipetter as defined in claim 5 further characterized by:
said cylinders extending out of the case at the bottom of the grip.

18. A pipetter as defined in claim 14 wherein upon actuation,
the piston plate moves translationally less than half the distance of the translational movement of the slide.

* * * * *